US008963097B2

(12) United States Patent
Levene

(10) Patent No.: US 8,963,097 B2
(45) Date of Patent: Feb. 24, 2015

(54) METHOD FOR PRODUCING A SCINTILLATOR ARRAY WITH SILVER (AG) BASED SPACERS

(75) Inventor: Simha Levene, D.N. Hanegev (IL)

(73) Assignee: Koninklijke Philips N.V., Eindhoven (NL)

( * ) Notice: Subject to any disclaimer, the term of this patent is extended or adjusted under 35 U.S.C. 154(b) by 306 days.

(21) Appl. No.: 13/808,158

(22) PCT Filed: Jun. 24, 2011

(86) PCT No.: PCT/IB2011/052772
§ 371 (c)(1), (2), (4) Date: Jan. 3, 2013

(87) PCT Pub. No.: WO2012/004703
PCT Pub. Date: Jan. 12, 2012

(65) Prior Publication Data

US 2013/0108008 A1 May 2, 2013

Related U.S. Application Data

(60) Provisional application No. 61/361,662, filed on Jul. 6, 2010.

(51) Int. Cl.
*G01T 1/24* (2006.01)
*G01T 1/20* (2006.01)
(Continued)

(52) U.S. Cl.
CPC ................. *A61B 6/40* (2013.01); *G01T 1/2002* (2013.01); *G10K 15/00* (2013.01); *A61B 6/032* (2013.01); *A61B 6/4233* (2013.01)
USPC .................. 250/370.11; 250/361 R; 250/367; 250/484.4; 156/247; 378/19; 427/162

(58) Field of Classification Search
CPC ......... A61B 6/40; A61B 6/032; A61B 6/4233
USPC ................ 378/19; 156/247; 250/370.11, 367, 250/361 R, 484.4; 427/162
See application file for complete search history.

(56) References Cited

U.S. PATENT DOCUMENTS 6,245,184 B1 * 6/2001 Riedner et al. ................ 156/247
6,252,927 B1 * 6/2001 Wieczorek et al. ............. 378/19
(Continued)

FOREIGN PATENT DOCUMENTS

EP 1995608 A1 11/2008

OTHER PUBLICATIONS

Sauereisen, High Temperature Ceramic Cements Engineered for Performance, 2001, 6 pages, http://www.sauereisen.com/pdf/HIGHTEMP.pdf.
(Continued)

*Primary Examiner* — Nikita Wells

(57) ABSTRACT

A method includes obtaining a plurality of the two dimensional arrays of gadolinium oxysulfide. An array has wider width non-silver based spacers (304) that extend between rows or columns of dixels and narrower width non-silver based spacers (306) that extend between the other of the rows or columns of dixels. The method further includes applying a silver coating (312) to at least one of a top or bottom surface of the arrays. The method further includes forming a stack by stacking the silver coated arrays, one on top of another (FIG. 3B), with substantially equal layers of adhesive between adjacent arrays. The method further includes slicing the stack through the wider non-silver based spacers to form two dimensional arrays of scintillator dixels (314) having silver based spacers (312) along at least one direction of the array.

21 Claims, 5 Drawing Sheets

(51) Int. Cl.

| | |
|---|---|
| ***A61B 6/00*** | (2006.01) |
| ***G10K 15/00*** | (2006.01) |
| *A61B 6/03* | (2006.01) |

(56) References Cited

U.S. PATENT DOCUMENTS

| | | | | |
|---|---|---|---|---|
| 6,344,649 | B2 | 2/2002 | Riedner et al. | |
| 7,573,035 | B2 | 8/2009 | Levene et al. | |
| 2001/0011709 | A1 | 8/2001 | Riedner et al. | |
| 2002/0054954 | A1 | 5/2002 | Otto | |
| 2002/0181647 | A1 | 12/2002 | Venkataramani et al. | |
| 2004/0174952 | A1 | 9/2004 | Hoffman | |
| 2010/0264322 | A1* | 10/2010 | Levene et al. | 250/367 |
| 2011/0108733 | A1* | 5/2011 | Menge | 250/370.08 |
| 2012/0001078 | A1* | 1/2012 | McEvoy et al. | 250/366 |

OTHER PUBLICATIONS

Allen et al., Electrical sintering of nanoparticle structures, Nanotechnology, 2008, 4 pages, vol. 19, No. 175201, http://iopscience.iop.org/0957-4484/19/17/175201/pdf/0957-4484_19_17_175201.pdf.

Advanced Nano Products, Nano Silver Ink & Past product index, downloaded Jun. 30, 2010, 2 pages, http://www.anapro.com/english/product/nano-silver-ink.asp.

* cited by examiner

METHOD FOR PRODUCING A SCINTILLATOR ARRAY WITH SILVER (AG) BASED SPACERS

CROSS REFERENCE TO RELATED APPLICATIONS

This application is a national filing of PCT application Serial No. PCT/IB2011/052772, filed Jun. 24, 2011, published as WO 2012/004703 A2 on Jan. 12, 2012, which claims the benefit of U.S. provisional application Ser. No. 61/361,662 filed Jul. 6, 2010, which is incorporated herein by reference.

The following generally relates to scintillators and more particularly to a method of producing a scintillator array with silver (Ag) based spacers along at least one direction of the scintillator array. The scintillator array can be used with various imaging modalities such as computed tomography (CT), x-ray, and/or other imaging modalities.

A computed tomography (CT) system includes a radiation source that rotates about and emits radiation that traverses an examination region, and a radiation-sensitive detector array which detects the radiation that traverses the examination region. The detector array has included a scintillator array coupled to a photosensor array. The scintillator array receives the radiation and converts it to light indicative thereof, and the photosensor array receives the light and produces an electrical signal indicative thereof. The signal can be reconstructed to generate volumetric image data indicative of a scanned object or subject disposed in the examination region.

A conventional scintillator array has included an array of scintillator dixels (detector pixels) separated by reflective spacers. The spacers for a particular dixel direct light produced in that dixel to a corresponding light receiving region of the photosensor array and mitigate inter-dixel (optical) cross talk. Traditionally, such spacers are made of white scattering composite material formed by dispersing titanium dioxide ($TiO_2$) pigment in a suitable epoxy resin. Detector array spatial resolution can be increased by reducing dixel size, but it is then generally desirable to reduce the thickness of the white spacers in proportion, in order to preserve the radiation QDE (quantum detection efficiency) of the detector array. Unfortunately, thinner $TiO_2$ based spacers have less reflectance relative to thicker $TiO_2$ based spacers, and this may decrease radiation absorption efficiency and increase inter-dixel cross-talk.

Very thin separators formed from bright silver (Ag) can provide adequate reflectance and substantially reduce inter-dixel cross-talk. They can be formed on the smoothed surface of a flat scintillator array by printing nano-particulate silver ink on the surface, and afterwards annealing the ink, which smoothes its surface, removes stippling and forms a bright coating with high reflectance. A plurality of such arrays can then be stacked and glued to form a block, and then sliced to make arrays with very thin silver spacers. However, the above-noted process is not well-suited for GOS ($Gd_2O_2S$, or gadolinium oxysulfide) scintillators because the slicing process causes mechanical damage to the surface layer of the GOS scintillator. The damage can be repaired by annealing the slices at temperatures above 700° C. (Celsius). Unfortunately, such a temperature will break down and destroy the glue holding the array together.

Aspects of the present application address the above-referenced matters and others.

According to one aspect, a method includes obtaining a plurality of the two dimensional arrays of gadolinium oxysulfide. An array has wider width non-silver based spacers that extend between rows or columns of dixels and narrower width non-silver based spacers that extend between the other of the rows or columns of dixels. The method further includes applying a bright silver coating to at least one of a top or bottom surface of the arrays. The method further includes forming a stack by stacking the silver coated arrays, one on top of another, with substantially equal thin layers of adhesive between adjacent layers. The method further includes slicing the stack through the wider non-silver based spacers to form two dimensional arrays of scintillator dixels having silver based spacers along at least one direction of the array.

In another aspect, a method includes stacking silver coated arrays, one on top of another, with substantially equal thin layers of adhesive between adjacent layers. The adhesive withstands temperatures of up to 850° C. The method further includes slicing the stack substantially perpendicular to the arrays. The method further includes mechanically flattening and smoothing and applying a bright silver coating to the stack slices. The method further includes stacking the silver coated slices, one on top of another, with substantially equal thin layers of the high-temperature adhesive between adjacent layers. The method further includes slicing the silver coated stack substantially perpendicular to the silver coated slices, forming two dimensional arrays of scintillators having silver based spacers extending along rows and columns of dixels of the arrays. The method further includes annealing the arrays at a temperature in a range of 700-850° C.

In another aspect, a method includes obtaining a plurality of the two dimensional arrays of gadolinium oxysulfide. The arrays have first non-silver based spacers with first wider widths that extend between rows or columns of dixels and second non-silver based spacers with second narrower widths that extend between the other of the rows or columns of dixels. The method further includes removing any reflective material on outer surfaces of the arrays. The method further includes mechanically flattening and smoothing top and bottom surfaces of the arrays. The method further includes applying a silver coating to at least one side of the arrays, and drying and annealing the silver coating to form a bright silver coating. The method further includes stacking the silver coated arrays, one on top of another, with substantially equal layers of adhesive between adjacent layers. The method further includes compressing the stack to a predetermined thickness. The method further includes expressing excess adhesive at sides of compressed stack, leaving very thin layers of adhesive. The method further includes curing the adhesive. The method further includes slicing the stack through the wider reflective spacers. The method further includes removing residual non-silver spacer on cut sides of the slices, to form two dimensional arrays of scintillator dixels having silver based spacers between the layers of the two dimensional array of scintillator dixels.

Still further aspects of the present invention will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
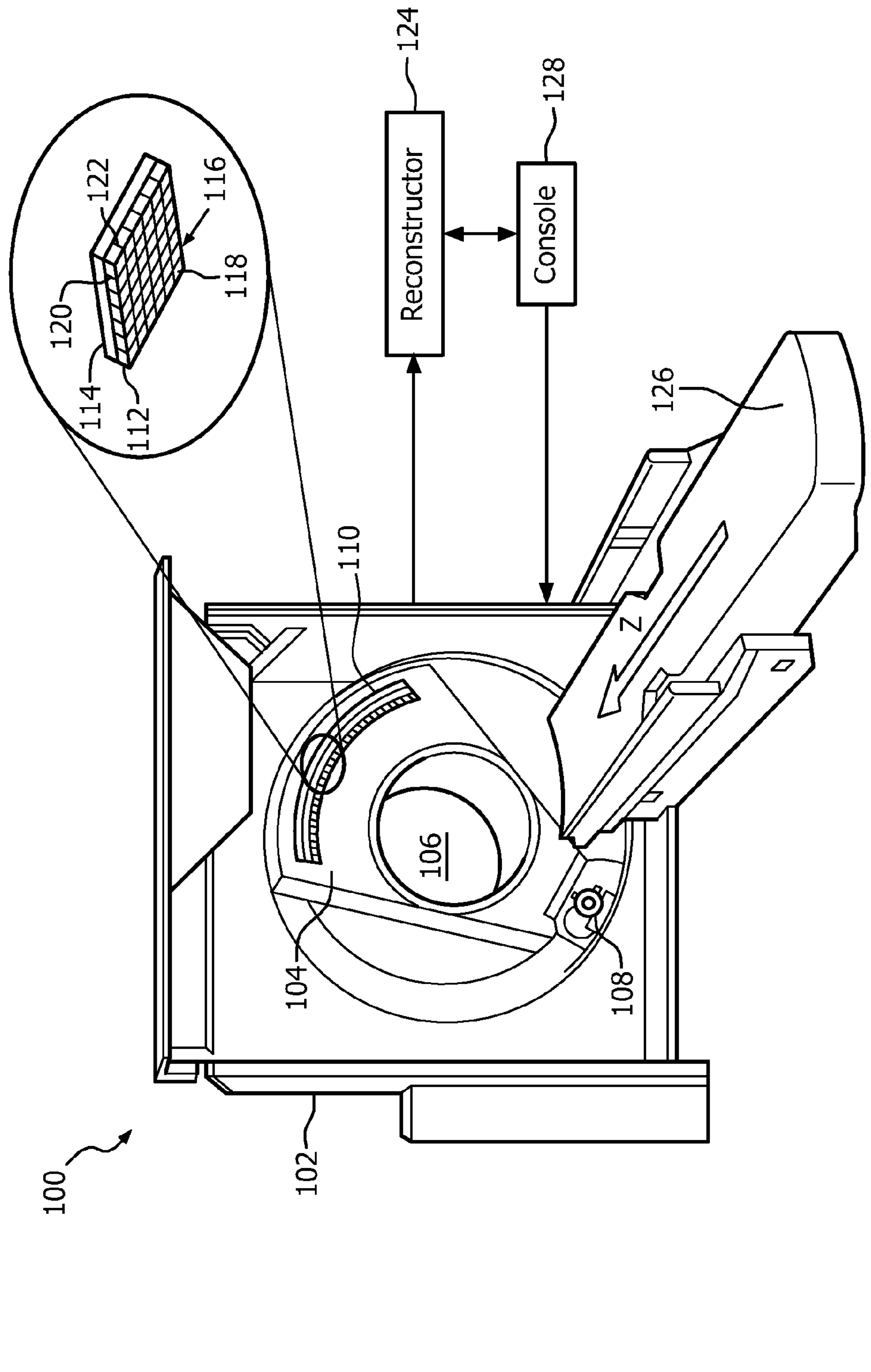
FIG. 1 illustrates an example imaging system with a two-dimensional detector array including a two-dimensional scintillator array with silver based spacers along at least one direction of the scintillator array.

FIG. 1 illustrates an imaging system 100, such as a computed tomography (CT) system, that includes a stationary gantry portion 102 and a rotating gantry portion 104. The rotating gantry portion 104 is rotatably supported by the stationary gantry portion 102 and is configured to rotate about an examination region 106 around a longitudinal or z-axis. The rotating gantry portion 104 supports an x-ray source 108, such as an x-ray tube, that rotates with the rotating gantry portion 104 about the examination region 106 and generates and emits radiation that traverses the examination region 106.

A radiation-sensitive detector array 110 includes a plurality of scintillator arrays 112 each optically coupled to a photosensor array 114. Each scintillator array 112 detects radiation that traverses the examination region 106 and generates an optical signal indicative of the detected radiation, and the photosensor arrays 114 receive the light and generate signals indicative of the light and hence of the detected radiation. In the illustrated embodiment, the scintillator array 112 includes a plurality of rows 116 of scintillator dixels 118. The rows 116 of dixels 118 are separated by spacers 120, and the individual dixels 118 along each row 116 are separated by spacers 122. The spacers 120 and 122 include a reflective material. The reflective material facilitates directing light produced by a dixel 118 to a corresponding light-sensing region of the photosensor array 114 and/or mitigating inter-dixel (optical) cross-talk, relative to a configuration in which the spacers 120 and/or 122 do not include a reflective material. Suitable reflective materials may include but are not limited to white, scattering composites, for example, $TiO_2$ powder dispersed in a clear resin, and may include bright mirrors, and for example, silver (Ag) formed on a smooth surface.

In one embodiment, the detector array 110 is configured as a high resolution detector and has relatively small scintillator dixels 118. A non-limiting example dixel 118 geometry is about 0.75-1.25 mm by 0.75-1.25 mm by 1.3-2.0 mm thick, such as 0.70 mm by 1.1 mm by 1.3-2.0 mm thick. Of course other geometries, including larger and smaller volumes, non-cubic geometries, etc. are also contemplated herein. In the illustrated embodiment, at least one of the spacers 120 or 122 includes sliver, and the silver based spacer(s) has a width in a range of about 10-75 microns such as, for example, 20-50 microns or other range, A non-limiting example spacer comprises a bright silver of thickness about 0.5 microns-5 microns such as 0.8-1.3 microns. Where only one of the spacers 120 or 122 includes silver, the non-silver based spacer 120 or 122 has a width in a range of about 65-135 microns such as, for example, 75-125 microns or other range.

A reconstructor 124 reconstructs the signal produced by the detector arrays 110 and generates volumetric image data indicative of an object or subject in the examination region 106. A suitable reconstruction algorithm includes, but is not limited to, a high resolution reconstruction algorithm. A support 126 such as a couch supports a patient or object in the examination region 106. The support 126 is movable so as to guide the object or subject with respect to the examination region 106 in the x, y, and z directions.

A computer serves as an operator console 128. The console 128 includes a human readable output device such as a monitor or display and an input device such as a keyboard and mouse. Software resident on the console allows the operator to control and interact with the scanner 100, for example, allowing an operator to select a high resolution or other scan protocol.

Figure 2:
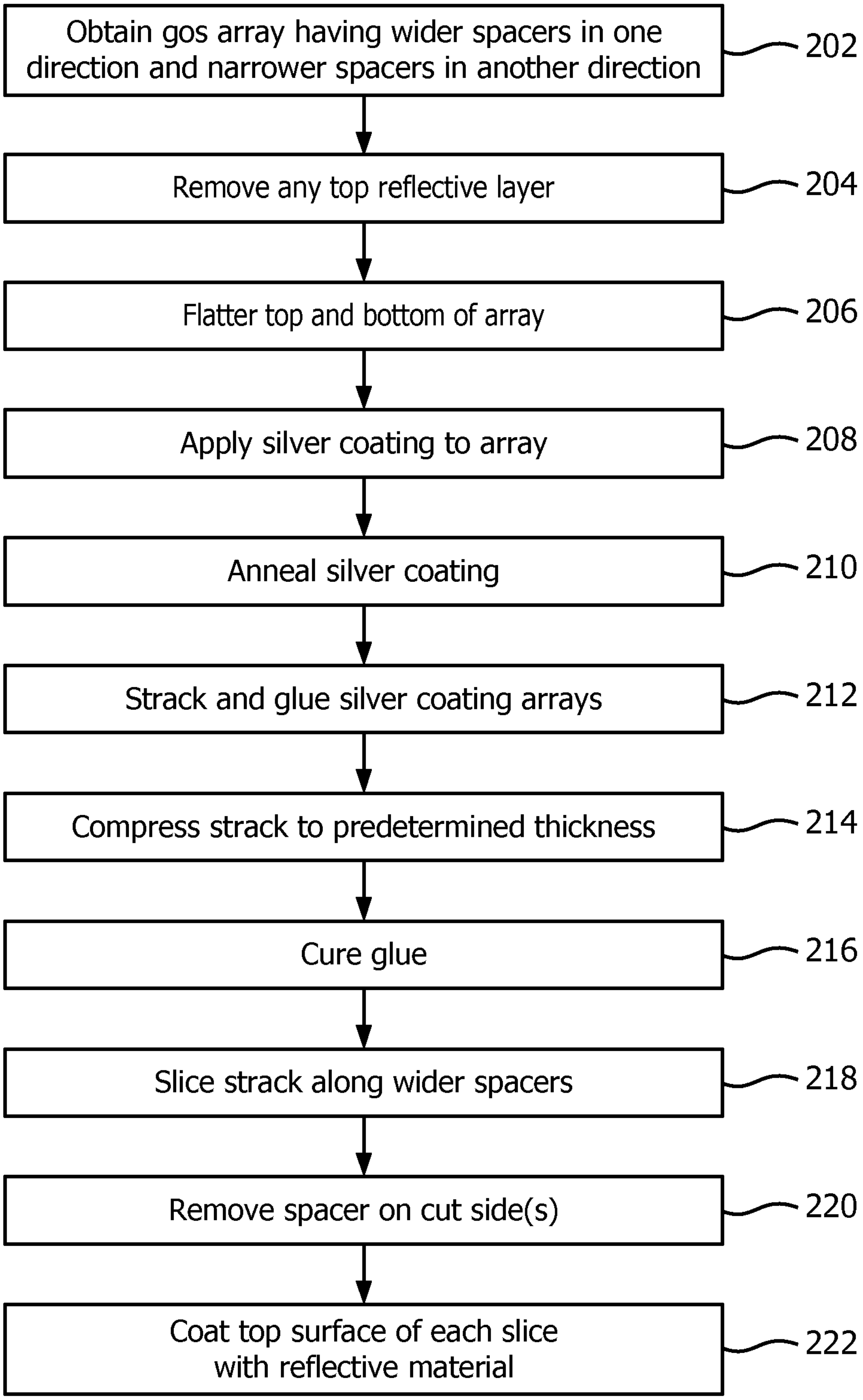
FIGS. 2 and 3 illustrate a method for producing a two-dimensional scintillator array having silver based spacers along one direction.
Figure 3:
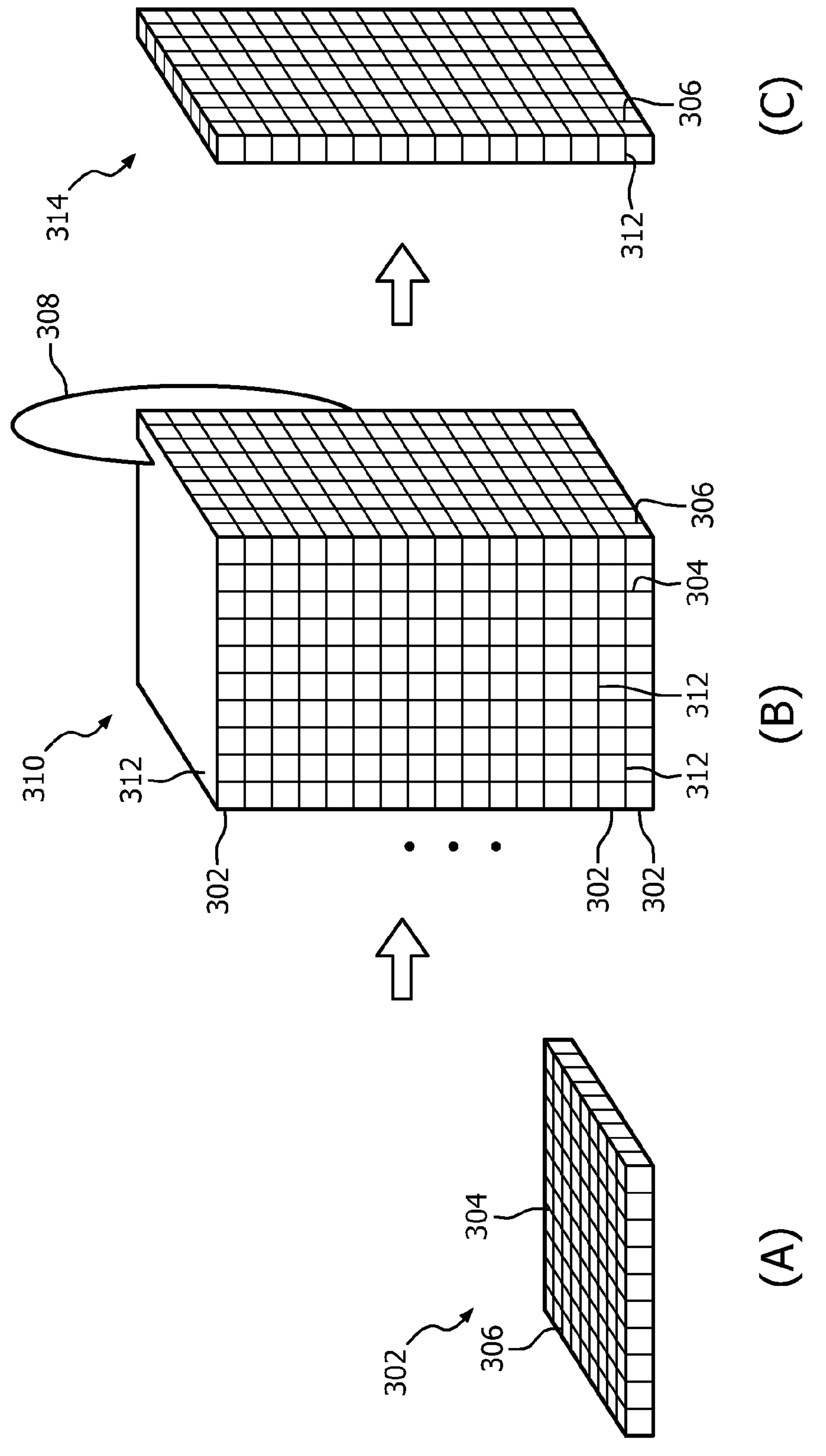
Figure 4:
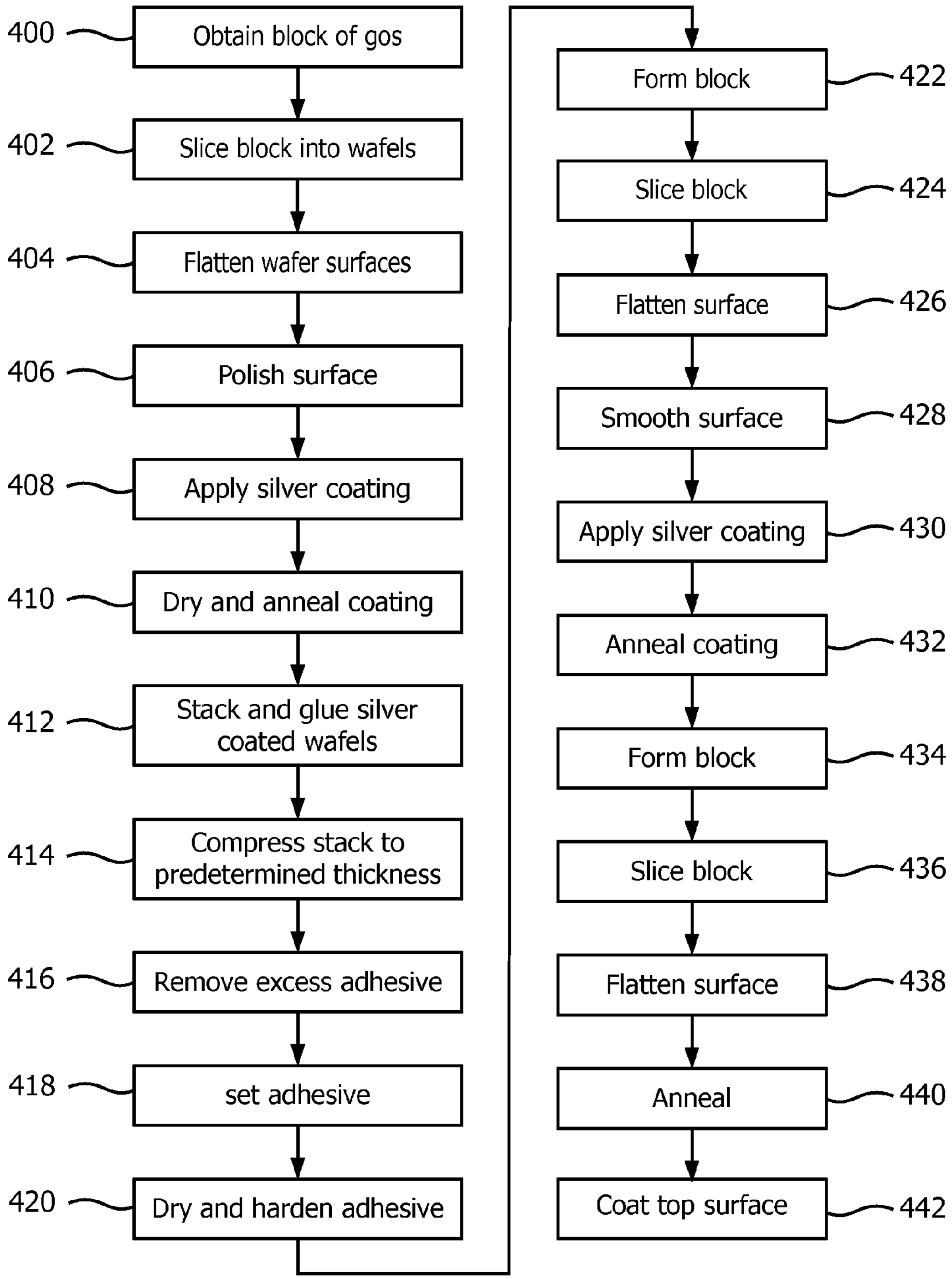
FIGS. 4-10 illustrate a method for producing a two-dimensional scintillator array having silver based spacers along multiple directions.

FIGS. 2 and 3 illustrate a method for producing a two-dimensional (2D) scintillator array 212 having silver based spacers along one direction of the array.

At 202, an array of annealed GOS with relatively wider white reflective (e.g., white resin) spacers in one direction and narrower reflective spacers in the other direction is obtained. The array can be produced using any established or other technology.

FIG. 3(A) illustrates an example of such an array 302 with wide spacers 304 having a width in a range of about 100-400 microns and narrow spacers 306 having a width in a range of about 70-125 microns.

Returning to FIG. 2, at 204, if the array of annealed GOS includes a top layer of white reflector, the top layer can be removed.

At 206, the top and bottom of the array are flattened, and optionally smoothed. The flattening can be achieved via polishing or other technique. In the illustrated example, the array is flattened to about ±10 microns.

At 208, the array is coated with a silver coating. Such a coating can be applied by vacuum sputtering but it is best to use a nano-particulate silver ink. Non-limiting examples of such an ink include, but are not limited to, silver nano-paste DGP (with nano-particle diameters of 5-10 nm), a product of Advanced Nano Products Co., Ltd of Korea, and TEC-CO-010 containing 10% Ag, a product of Inktec Co., Ltd of Korea. The array can be spray coated with a primer, dried, spray coated with the nano-particulate silver ink, and then dried, for example, for five (5) minutes at 130° C.

At 210, the silver coating is annealed. In one instance, the silver coating is annealed in an oven, for example, with a temperature in a range of about 150-200° C., such as about 175° C. In another instance, the silver coating is annealed at room temperature. A suitable room temperature annealing using inductive heating is described in Allen et al, "Electrical sintering of nanoparticle structures," Nanotechnology 19, 2008, 175201, or microwave heating. Using inductive and/or microwave heating may help smooth the silver coating without exposing the array to high temperatures which may damage or distort the adhesives or mar the silver.

At 212, a plurality of the silver coated arrays is stacked, one on top of another, with substantially equal layers of liquid glue between adjacent layers. It is not necessary to use an optically transparent glue for this purpose. The stack may include 2, 4, 16, 32, 128, and/or other number of arrays.

At 214, the stack is compressed to a predetermined thickness. For example, the stack can be compressed to the required nominal thickness with a tolerance of about ±20 microns. Excess glue will express at the sides.

At 216, the glue is cured, for example, permissibly at room temperature.

At 218, the stack is sliced along the wider reflective spacers. Various cutting devices can be used such as a high-speed rotary saw, a wire saw, a multi-wire saw, and/or other cutting device.

FIG. 3(B) shows an approach in which a rotary saw 308 cuts through the wider spacers 304 of a stack 310 of the arrays 302 with the silver 312 coating.

Returning to FIG. 2, at 220, any residual spacer on the cut side(s) of the slice is removed. This can be done through rubbing down, scraping, or other approach, without damaging the surface of the GOS.

At 222, the top surface of each slice can be coated with reflective silver and/or white resin.

FIG. 3(C) shows a slice 314 with silver spacers 312 along a first direction and white resin reflective spacers 306 along a second direction, which is generally perpendicular to the first direction. With the illustrated slice, the silver based spacers have a width in a range of about 25-50 microns, in which the silver itself is about 1 micron thick, and white resin spacers have widths in a range of about 75-125 microns. The geometric quantum detection efficiency of the array 314 is greater than 80% such as 88% and may be as high as 90%

FIGS. 4-10 illustrate a method for producing a two-dimensional (2D) scintillator array 212 having silver based spacers along multiple directions of the array.

At 400, a block of GOS is obtained.

At 402, the block is sliced into wafers. The block can be sliced using micro-electronics silicon technology, a rotary saw, a wire saw, a multi-wire saw with aqueous diamond-loaded cutting fluids, and/or otherwise. In one embodiment, the slices are about 1 mm thick or otherwise.

At 404, the surface of the arrays is flattened. This can be achieved through grinding or otherwise. In one instance, the surface is ground to less than 5 microns, which may help ensure a thin glue line.

At 406, the flattened surfaces are polished. This may facilitate ensuring a smooth, reflective surface At 408, the polished surfaces are coated with silver. In one instance, this includes spray coating the surface with nano-particulate silver as described herein. By glazing the top and bottom of the arrays using a silicate glazing "slip" or diluted Fortafix Autostic FC4, a product of Minco UK Ltd. of Wisconsin, USA, and afterwards drying and baking to glazing temperature, oxidation of the silver by excess free S in the $Gd_2O_2S$ (which can cause the silver to turn black) can be mitigated. The "slip" should be dilute enough so that any excess can be spun off. Otherwise, the "slip" may be ground down after glazing to reduce the thickness and avoid excess inter-array spacing.

At 410, the coating is dried and annealed. By way of example, the coating can be dried for five (5) or so minutes at a temperature in a range of 100° C. to 160° C. such as 140° C., 130° C., etc. This may facilitate forming a bright reflective silver coating on the top and bottom faces of the arrays.

Figure 5:
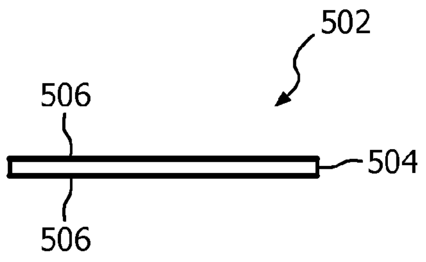

FIG. 5 illustrates an example coated array 502, including an array 504 with silver based coatings 506.

Returning to FIG. 4, at 412, the silvered arrays are stacked to form a block with adjacent arrays separated by a layer of adhesive. A suitable adhesive is an adhesive that can withstand GOS annealing temperatures, such as adhesives that withstand temperature up to 850° C. without breaking down or being destroyed. For example, the adhesive may be a silicate adhesive such as single-component Fortafix Autostic FC4, a two-component Fortafix TC2 (a product of Minco UK Ltd.), a zirconia based adhesive, or other adhesive.

Some ceramic cements do not adhere well to smooth silver coatings and thus when using such a cement a silicate joining layer can be formed using TEOS spray, and dried and glazed at 1100° C. The glazing process can also anneal the GOS, repairing surface damage due to slicing and polishing, and the impervious layer of glazing will prevent subsequent oxidation of the Ag coating by sulfide in the GOS.

At 414, the stack is compressed to about a predetermined height. For example, in one embodiment the stack is compressed to about ±20 microns about a predetermined height.

At 416, excess adhesive expressed at the edges is removed. This adhesive can be removed manually, via air-jet wiping, and/or otherwise.

At 418, the adhesive is set. In one instance, adhesive is warmed to a temperature in a range of about 50 to 90° C. such as 75° C. The adhesive is warmed long enough for excess moisture to diffuse outwardly through the adhesive line. This may take several hours to several days, or other time duration.

At 420, the adhesive is dried and hardened if it contains excess moisture. This can be achieved by heating the stack slowly to about 300° C. and baking for several hours.

At 422, an array block is formed. This can be achieved by baking the stack to 700° C.-900° C., which firms and sets the glaze, which will "pot" the silvered arrays together in a strong (rather brittle) ceramic block.

At 424, the solid block is cut into slices. The slices can be cut using micro-electronics silicon technology, a rotary saw, a wire saw, a multi-wire saw with aqueous diamond-loaded cutting fluids, and/or otherwise. In one embodiment, the slices are about 1 mm thick or otherwise, according to the spatial resolution required in the CT image.

Figure 6:
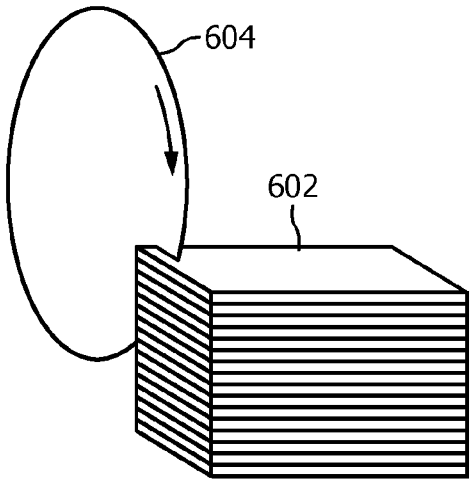
Figure 7:
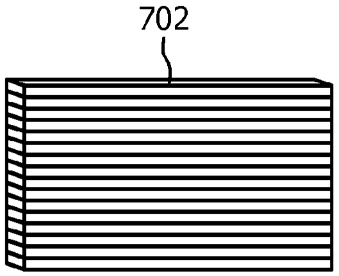

FIG. 6 illustrates an example in which a block 602 is cut using a rotary saw 604, and FIG. 7 illustrates an example cut slice 702.

Returning to FIG. 4, at 426, the surface of each slice is flattened. For example, the surface can be ground to flatten it to less than 10 g to ensure a thin glue line.

At 428, the flattened slices are smoothed. This can be achieved through polishing.

At 430, the slices are coated with silver. For example, the slices can be spray coated with nano-particulate silver as described herein.

At 432, the silver coating is annealed. For example, the coated slices can be dried for several minutes as described herein.

Figure 8:
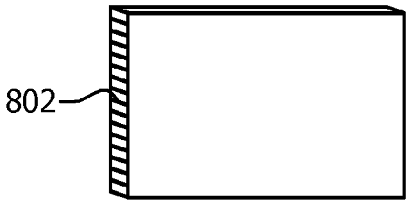

FIG. 8 illustrates an example annealed silver coated slice 802.

Returning to FIG. 4, at 434, the silvered slices are stacked and set to form a block. The block may include 4, 16, 32, etc. slices, and are separated by minimally thick layers of the high-temperature adhesive.

At 436, the block is sliced. In this embodiment, the slices are about 1-2 mm thick. The slices may be cut using micro-electronics silicon technology, using rotary and wire saws using diamond-loaded cutting fluids.

Figure 9:
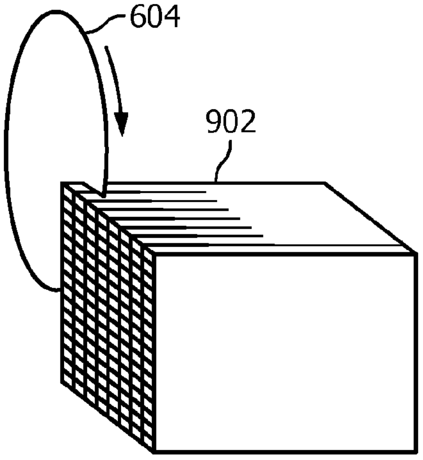

FIG. 9 illustrates an example in which a block 902 is cut using the rotary saw 604.

At 438, the top and bottom surfaces of the slices are flattened and smoothed At 440, the slices are annealed. For example, in one instance, the slices are annealed at 700-850° C. in an inert atmosphere, vacuum, or the like. This may repair the machining damage caused to the GOS, without damaging the nano-particulate silver layer.

At 442, the top surface of the slices is coated. In one instance, the top is coated with a layer of white reflective epoxy. In another instance, the top is smoothed and coated with a bright silver layer.

Figure 10:
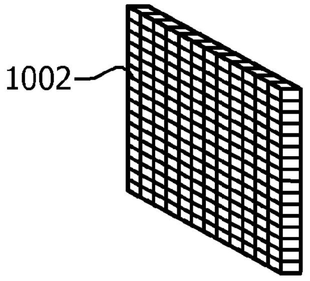

FIG. 10 illustrates an example of a resulting scintillator array 1002. The illustrated scintillator array 1002 is about 0.75-1.25 mm by 0.75-1.25 mm by 1.3-2 mm thick (depending upon the spatial resolution required in the CT image) with silver based separators of about 25-50 microns wide.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A method, comprising:

obtaining a plurality of the two dimensional arrays of gadolinium oxysulfide, wherein an array has wider width non-silver based spacers that extend between rows or columns of dixels and narrower width non-silver based spacers that extend between the other of the rows or columns of dixels;

applying a silver coating to at least one of a top or bottom surface of the arrays;

forming a stack by stacking the silver coated arrays, one on top of another, with substantially equal layers of adhesive between adjacent layers; and slicing the stack through the wider non-silver based spacers to form two dimensional arrays of scintillator dixels having silver based spacers along at least one direction of the array.

2. The method of claim 1, further comprising:

removing residual wider width non-silver based spacer from the arrays of scintillator dixels having silver based spacers along at least one direction of the array.

3. The method of claim 2, further comprising:

applying a reflective coating to a top surface of the arrays of scintillator dixels having silver based spacers along at least one direction of the array.

4. The method of claim 3, wherein the reflective coating is one of a white resin or a silver based coating.

5. The method of claim 1, further comprising:

flattening and smoothing top and bottom surfaces of the two dimensional arrays of gadolinium oxysulfide, with wider width non-silver based spacers that extend between rows or columns of dixels and narrower width non-silver based spacers that extend between the other of the rows or columns of dixels prior to applying the silver coating.

6. The method of claim 1, further comprising:

compressing the stack to a predetermined thickness prior to curing the adhesive and slicing the stack.

7. The method of 1, wherein the slicing does not cause surface damage to the arrays.

8. The method of claim 1, wherein the silver based spacers have a width in a range of 15 to 60 microns.

9. The method of claim 8, wherein the silver based spacers have a width in a range of 25 to 50 microns.

10. The method of claim 9, wherein the arrays have non-silver based spacers along a direction substantially perpendicular to the direction of the silver based spacers.

11. The method of claim 10, wherein the non-silver based spacers have a width in a range of about 70 to 125 microns.

12. The method of claim 1, further comprising:

optically coupling the array to a photosensor array of a radiation sensitive detector array of an imaging system.

13. A method, comprising:

stacking silver coated wafers of gadolinium oxysulfide scintillator, one on top of another, with substantially equal layers of adhesive between adjacent layers, wherein the adhesive withstands temperatures of up to 850° C.;

slicing the stack substantially perpendicular to the wafers;

smoothing and applying a silver coating to the stack slices;

stacking the silver coated arrays, one on top of another, with substantially equal layers of the adhesive between adjacent arrays;

slicing the silver coated stack substantially perpendicular to the silver coated slices, forming two dimensional arrays of scintillators having silver based spacers extending along rows and columns of dixels of the arrays; and annealing the arrays at a temperature in a range of 700-850° C.

14. The method of claim 13, father comprising:

applying a reflective coating to a top side of the annealed arrays.

15. The method of claim 13, wherein the array includes scintillator dixels having dimensions of about 0.8-1.25 mm by 0.8-1.25 mm by 1.3-2.0 mm thick.

16. The method claim 13, wherein the array has an x-ray absorption efficiency greater than 89%.

17. The method of claim 13, wherein the adhesive includes high temperature ceramic glue.

18. The method of claim 13, wherein the adhesive includes high temperature silicate adhesive.

19. The method of claim 13, wherein the adhesive includes high temperature zirconia adhesive.

20. A method, comprising:

obtaining a plurality of the two dimensional arrays of gadolinium oxysulfide, wherein the arrays have first non-silver based spacers with First wider widths that extend between rows or columns of dixels and second non-silver based spacers with second narrower widths that extend between the other of the rows or columns of dixels;

removing any reflective material on outer surfaces of the arrays;

flattening and smoothening top and bottom surfaces of the annealed arrays;

applying a silver coating to at least one side of the arrays;

drying and annealing the silver coating;

stacking the silver coated arrays, one on top of another, with substantially equal layers of adhesive between adjacent layers;

compressing the stack to a predetermined thickness;

expressing excess adhesive at sides of compressed stack;

curing the adhesive;

slicing the stack through the wider reflective spacers; and removing residual non-silver spacer on cut sides of the slices to form two dimensional arrays of scintillator dixels having silver based spacers between the layers of the two dimensional array of scintillator dixels.

21. A CT scanner comprising detector arrays formed according to claim 1.

* * * * *